United States Patent
Boday et al.

(10) Patent No.: US 10,059,727 B2
(45) Date of Patent: Aug. 28, 2018

(54) FLAME RETARDANT FILLER

(71) Applicant: International Business Machines Corporation, Armonk, NY (US)

(72) Inventors: Dylan J. Boday, Tucson, AZ (US); Joseph Kuczynski, North Port, FL (US); Robert E. Meyer, III, Rochester, MN (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 15/831,454

(22) Filed: Dec. 5, 2017

(65) Prior Publication Data

US 2018/0094003 A1 Apr. 5, 2018

Related U.S. Application Data

(60) Division of application No. 15/015,905, filed on Feb. 4, 2016, which is a continuation of application No.
(Continued)

(51) Int. Cl.
*C07F 7/08* (2006.01)
*C07F 7/18* (2006.01)
(Continued)

(52) U.S. Cl.
CPC ............ *C07F 7/0878* (2013.01); *C07F 7/081* (2013.01); *C07F 7/0889* (2013.01);
(Continued)

(58) Field of Classification Search
CPC ........................................................ C07F 7/12
See application file for complete search history.

(56) References Cited

U.S. PATENT DOCUMENTS 3,686,930 A 8/1972 Kniebes et al.
3,748,827 A 7/1973 Bulian et al.
(Continued)

FOREIGN PATENT DOCUMENTS

DE 19857697 A1 6/2000
DE 102005056052 A1 5/2007
(Continued)

OTHER PUBLICATIONS

U.S. Appl. No. 13/204,009 to Boday et al., entitled "Microcapsules Adapted to Rupture in a Magnetic Field to Enable Easy Removal of One Substrate From Another for Enhanced Reworkability," filed Aug. 5, 2011.
(Continued)

Primary Examiner — Peter F Godenschwager
(74) Attorney, Agent, or Firm — Matthew J. Bussan

(57) ABSTRACT

A flame retardant filler having brominated silica particles, for example, imparts flame retardancy to manufactured articles such as printed circuit boards (PCBs), connectors, and other articles of manufacture that employ thermosetting plastics or thermoplastics. In this example, brominated silica particles serve both as a filler for rheology control (viscosity, flow, etc.) and a flame retardant. In an exemplary application, a PCB laminate stack-up includes conductive planes separated from each other by a dielectric material that includes a flame retardant filler comprised of brominated silica particles. In an exemplary method of synthesizing the brominated silica particles, a monomer having a brominated aromatic functional group is reacted with functionalized silica particles (e.g., isocyanate, vinyl, amine, or epoxy functionalized silica particles). Alternatively, a monomer having a brominated aromatic functional group may be reacted with a silane to produce a brominated alkoxysilane
(Continued)

monomer, which is then reacted with the surface of silica particles.

9 Claims, 5 Drawing Sheets

Related U.S. Application Data

14/512,491, filed on Oct. 13, 2014, now Pat. No. 9,303,047, which is a division of application No. 13/102,306, filed on May 6, 2011, now Pat. No. 8,900,491.

(51) Int. Cl.
| | |
|---|---|
| H05K 1/03 | (2006.01) |
| C08K 9/06 | (2006.01) |
| C08K 5/5465 | (2006.01) |
| C08K 5/5419 | (2006.01) |
| C07F 7/10 | (2006.01) |
| C08K 3/00 | (2018.01) |
| C08K 3/016 | (2018.01) |

(52) U.S. Cl.
CPC ............. *C07F 7/0896* (2013.01); *C07F 7/10* (2013.01); *C07F 7/1804* (2013.01); *C07F 7/1844* (2013.01); *C08K 5/5419* (2013.01); *C08K 5/5465* (2013.01); *C08K 9/06* (2013.01); *H05K 1/0373* (2013.01); *C08K 3/0058* (2013.01); *C08K 3/016* (2018.01); *H05K 2201/012* (2013.01); *H05K 2201/0209* (2013.01)

(56) References Cited

U.S. PATENT DOCUMENTS

| | | | |
|---|---|---|---|
| 3,936,976 A | 2/1976 | Porter et al. | |
| 3,956,179 A | 5/1976 | Sebestian et al. | |
| 4,115,081 A | 9/1978 | Ohno et al. | |
| 4,425,117 A | 1/1984 | Hugemann et al. | |
| 4,657,843 A | 4/1987 | Fukuyama et al. | |
| 4,670,299 A | 6/1987 | Fukuyama et al. | |
| 4,731,925 A | 3/1988 | Tanishi et al. | |
| 4,781,733 A | 11/1988 | Babcock et al. | |
| 4,904,632 A | 2/1990 | Pesek et al. | |
| 4,950,314 A | 8/1990 | Yamada et al. | |
| 4,965,062 A | 10/1990 | Van Dijk et al. | |
| 5,147,957 A | 9/1992 | Kumar | |
| 5,233,071 A | 8/1993 | Wilczek | |
| 5,286,280 A | 2/1994 | Chiou | |
| 5,733,663 A | 3/1998 | Scheunemann et al. | |
| 5,741,579 A | 4/1998 | Nishizawa | |
| 5,777,007 A | 7/1998 | Kagawa et al. | |
| 5,876,739 A | 3/1999 | Turnblad et al. | |
| 5,925,595 A | 7/1999 | Seitz et al. | |
| 6,001,943 A | 12/1999 | Enami et al. | |
| 6,060,530 A | 5/2000 | Chaouk et al. | |
| 6,165,253 A | 12/2000 | Sirkar et al. | |
| 6,339,166 B1 | 1/2002 | Allcock et al. | |
| 6,417,236 B1 | 7/2002 | Hobson et al. | |
| 6,514,439 B2 | 2/2003 | Van Koppenhagen et al. | |
| 6,673,246 B2 | 1/2004 | Markowitz et al. | |
| 6,682,751 B1 | 1/2004 | Hargrove et al. | |
| 6,710,181 B2 | 3/2004 | Kumagai et al. | |
| 6,744,269 B1 | 6/2004 | Johnson et al. | |
| 6,805,964 B2 | 10/2004 | Clouser et al. | |
| 6,858,634 B2 | 2/2005 | Asrar et al. | |
| 6,900,154 B2 * | 5/2005 | McCullough ............ B01J 27/12 502/104 | |
| 6,900,269 B2 | 5/2005 | Hwang et al. | |
| 6,972,249 B2 | 12/2005 | Akram et al. | |
| 6,986,943 B1 | 1/2006 | Cook et al. | |
| 7,056,522 B2 | 6/2006 | Voris et al. | |
| 7,101,394 B2 | 9/2006 | Hamm et al. | |
| 7,169,832 B2 | 1/2007 | Poppe et al. | |
| 7,211,192 B2 | 5/2007 | Shea et al. | |
| 7,553,901 B2 | 6/2009 | Horikoshi et al. | |
| 7,585,320 B2 | 9/2009 | Hamm et al. | |
| 7,687,722 B2 | 3/2010 | Japp et al. | |
| 7,759,406 B2 | 7/2010 | Kumon et al. | |
| 7,767,219 B2 | 8/2010 | Weber et al. | |
| 7,767,736 B2 | 8/2010 | Baran, Jr. | |
| 7,814,737 B2 | 10/2010 | Pierson | |
| 7,851,055 B2 | 12/2010 | Fukushima | |
| 8,741,804 B2 | 6/2014 | Boday et al. | |
| 9,186,641 B2 | 11/2015 | Boday et al. | |
| 9,434,133 B2 | 9/2016 | Boday et al. | |
| 2002/0014154 A1 | 2/2002 | Witzko et al. | |
| 2002/0026980 A1 | 3/2002 | Nakatani et al. | |
| 2002/0119317 A1 | 8/2002 | Gan et al. | |
| 2003/0020163 A1 | 1/2003 | Hung et al. | |
| 2003/0022791 A1 | 1/2003 | Asrar et al. | |
| 2003/0173255 A1 | 9/2003 | White et al. | |
| 2004/0062873 A1 | 4/2004 | Jung et al. | |
| 2004/0149127 A1 | 8/2004 | Lyons et al. | |
| 2006/0000766 A1 | 1/2006 | Ji | |
| 2006/0118490 A1 | 6/2006 | Landry et al. | |
| 2006/0276581 A1 | 12/2006 | Ratzsch et al. | |
| 2007/0023957 A1 | 2/2007 | Kotov et al. | |
| 2007/0164271 A1 | 7/2007 | Wait, Jr. | |
| 2007/0215004 A1 | 9/2007 | Kuroda et al. | |
| 2007/0241303 A1 | 10/2007 | Zhong et al. | |
| 2007/0251393 A1 | 11/2007 | Pope et al. | |
| 2007/0257091 A1 | 11/2007 | Kuczynski | |
| 2007/0270536 A1 | 11/2007 | Sachdev et al. | |
| 2008/0097014 A1 | 4/2008 | Park et al. | |
| 2008/0191729 A1 | 8/2008 | Blanco et al. | |
| 2008/0193543 A1 | 8/2008 | Morello et al. | |
| 2008/0210087 A1 | 9/2008 | Ku et al. | |
| 2008/0264563 A1 | 10/2008 | Kuczynski et al. | |
| 2009/0004488 A1 | 1/2009 | Park et al. | |
| 2009/0117373 A1 | 5/2009 | Wisniewski et al. | |
| 2009/0142638 A1 | 6/2009 | Katayama | |
| 2010/0027192 A1 | 2/2010 | Perry et al. | |
| 2010/0030185 A1 | 2/2010 | Hood et al. | |
| 2010/0234481 A1 | 9/2010 | Sugimoto et al. | |
| 2010/0240811 A1 | 9/2010 | He et al. | |
| 2010/0243520 A1 | 9/2010 | Glover et al. | |
| 2011/0092640 A1 | 4/2011 | Tzou | |
| 2011/0097416 A1 | 4/2011 | Nguyen et al. | |
| 2011/0189381 A1 | 8/2011 | Boday et al. | |
| 2012/0187046 A1 | 7/2012 | Boday et al. | |
| 2012/0256224 A1 | 10/2012 | Hatanaka et al. | |
| 2012/0279768 A1 | 11/2012 | Boday et al. | |
| 2013/0034739 A1 | 2/2013 | Boday et al. | |
| 2013/0109565 A1 | 5/2013 | Boday et al. | |
| 2013/0131244 A1 | 5/2013 | Dickens | |
| 2013/0337273 A1 | 12/2013 | Boday et al. | |

FOREIGN PATENT DOCUMENTS

| | | |
|---|---|---|
| EP | 0315836 A2 | 5/1989 |
| JP | 53-42181 A | 4/1978 |
| JP | 61144339 A | 7/1986 |
| JP | 2000297094 A | 10/2000 |
| JP | 2005197609 A | 7/2005 |
| WO | 2006/096033 A1 | 9/2006 |
| WO | 2011078010 A1 | 6/2011 |

OTHER PUBLICATIONS

U.S. Appl. No. 14/930,336, to Boday et al., entitled "Microcapsules Adapted to Rupture in a Magnetic Field to Enable Easy Removal of One Subtrate from Another for Enhanced Reworkability", filed Nov. 2, 2015, assigned to International Business Machines Corporation.
U.S. Appl. No. 15/207,016, to Boday et al., entitled "Microcapsules adapted to Rupture in a Magnetic Field to Enable Easy Removal of One Subtrate From Another for Enhanced Reworkability", filed Jul. 11, 2016, assigned to International Business Machines Corporation.
Shang-Hsiu Hu et al., "Controlled Rupture of Magnetic

(56) References Cited

OTHER PUBLICATIONS

Polyelectrolyte Microcapsules for Drug Delivery," Langmuir, vol. 24, No. 20, pp. 11811-11818, 2008.
B. J. Blaiszik et al., "Microcapsules filled with reactive solutions for self-healing materials," Polymer, vol. 50, pp. 990-997, 2009.
E. N. Brown et al., "In situ poly(urea-formaldehyde) microencapsulation of dicyclopentadiene," Journal of Microencapsulation, vol. 20, No. 6, pp. 719-730, 2003.
M. Yamaura et al., "Preparation and characterization of (3-aminopropyl) triethoxysilane-coated magnetite nanoparticles," Journal of Magnetism and Magnetic Materials, vol. 279, pp. 210-217, 2004.
S. F. Peteu et al., "Responsive Polymers for Crop Protection," Polymers, vol. 2, pp. 229-251, Aug. 19, 2010.
J. Liu et al., "Magnetically Sensitive Alginate-Templated Polyelectrolyte Multilayer Microcapsules for Controlled Release of Doxorubicin," Journal of Physical Chemistry C, vol. 114, No. 17, pp. 7673-7679, Apr. 14, 2010.
M. Alley et al., "Pop-up and/or Starter Fertilizers for Corn," Virginia Cooperative Extension Publication 3002-1438, pp. 1-5, 2010.
Guoliang Zhang, E.L. Cussler, "Hollow fibers as structured distillation packing", Journal of Membrane Science, vol. 215, Issues 1-2, Apr. 15, 2003, pp. 185-193.
J. Andrieu, "Influence of Wettability on Liquid Phase Texture in a Countercurrently Irrigated Packing", Chemical Engineering Science, vol. 30, 1975, pp. 217-220.
Barry S. Hindin, "Silver Sulfide Corrosion Control Using Corrosion Prevention Compounds", Corrosion 2006, Mar. 12-16, 2006, San Diego, California, Paper No. 06264, Copyright 2006, NACE International.
English translation of DE 19857697 A1, Jun. 15, 2000.
U.S. Appl. No. 12/696,328, to Boday et al., entitled "Anti-Corrosion Conformal Coating for Metal Conductors Electrically Connecting an Electronic Circuit", filed Jan. 29, 2010, assigned to International Business Machines Corporation.
Wikipedia contributors, "Natural gas processing", Wikipedia, The Free Encyclopedia, http://en.wikipedia.org/w/index.php?title=Natural_gas_processing&oldid=400027904 (accessed Dec. 13, 2010), pp. 1-7.
Wikipedia contributors, "Silsesquioxane", Wikipedia, The Free Encyclopedia, http://en.wikipedia.org/w/index.php?title=Silsesquioxane&oldid=402217379 (accessed Dec. 13, 2010), pp. 1-9.
"UCARSOL GT 10 Antifoam", Product Information, Gas Treating Products & Services, The Dow Chemical Company, Midland, Michigan, Published Jul. 2004, pp. 1-4. (Available at http://www.dow.com/gastreating/solution/ngp_osr.htm).
King, David L., et al., "Removal of Sulfur Components from Low Sulfur Gasoline Using Copper Exchanged Zeolite Y at Ambient Temperature", Pacific Northwest Laboratory, Richland, Washington, 2005, 1 page. (Available at http://iic.pnl.gov/abstracts/nacs/p_001.pdf).
"Hydrogen Sulfide Removal Methods", Excel Water Technologies, Inc., Fort Lauderdale, Florida, dated 2007, pp. 1-3. (Available at http://www.excelwater.com/eng/b2c/h2s.php).
I. Manconi et al., "Removal of H2S and Voltatile Organic Sulfur Compounds by Silicone Membrane Extraction", Research Article, Society of Chemical Industry, Aug. 4, 2008, pp. 69-77.
U.S. Appl. No. 13/010,995, to Boday et al., entitled "Silicone-Based Chemical Filter and Silicone-Based Chemical Bath for Removing Sulfur Contaminants", filed Jan. 21, 2011, assigned to International Business Machines Corporation.
U.S. Appl. No. 13/802,543, to Boday et al., entitled "Silicone-Based Chemical Filter and Silicone-Based Chemical Bath for Removing Sulfur Contaminants", filed Mar. 13, 2013, assigned to International Business Machines Corporation.
U.S. Appl. No. 13/802,652, to Boday et al., entitled "Silicone-Based Chemical Filter and Silicone-Based Chemical Bath for Removing Sulfur Contaminants", filed Mar. 13, 2013, assigned to International Business Machines Corporation.

U.S. Appl. No. 15/044,150, to Boday et al., entitled "Removing Sulfur Contaminants From Water Using a Silicone-Based Chemical Filter", filed Feb. 16, 2016, assigned to International Business Machines Corporation.
U.S. Appl. No. 15/044,175, to Boday et al., entitled "Removing Sulfur Contaminants From a Fluid Using a Silicone-Based Chemical Filter", filed Feb. 16, 2016, assigned to International Business Machines Corporation.
Kumar et al., "Instantaneous, Facile and Selective Synthesis of Tetrabromobisphenol A using Potassium Tribromide: An Efficient Renewable Brominating Agent", Organic Process Research & Development, vol. 14, No. 1, 2010, pp. 174-179, Published on Web Dec. 20, 2009.
U.S. Appl. No. 13/102,306, to Boday et al., entitled "Flame Retardant Filler", filed May 6, 2011, assigned to International Business Machines Corporation.
U.S. Appl. No. 14/512,491, to Boday et al., entitled "Flame Retardant Filler", filed Oct. 13, 2014, assigned to International Business Machines Corporation.
U.S. Appl. No. 15/015,905, to Boday et al., entitled "Flame Retardant Filler", filed Feb. 4, 2016, assigned to International Business Machines Corporation.
U.S. Appl. No. 15/831,428, to Boday et al., entitled "Flame Retardant Filler", filed Dec. 5, 2017, assigned to International Business Machines Corporation.
U.S. Appl. No. 15/831,506, to Boday et al., entitled "Flame Retardant Filler", filed Dec. 5, 2017, assigned to International Business Machines Corporation.
"Flame Retardant Fact Sheet; Other Phosphorous Flame Retardants", European Flame Retardants Association, Sep. 28, 2011, 2 pages. (http://www.cefic-efra.com/images/stories/factsheet/7OtherPhosphorusFactSheetAB-1_00.pdf).
English Language Translation of Claims in CN101033327 (2007), 2 pages.
U.S. Appl. No. 13/397,010, to Boday et al., entitled "Non-Halogenated Flame Retardant Filler", filed Feb. 15, 2012, assigned to International Business Machines Corporation.
Dean et al., "Characterization of a Thermal Interface Material for Burn-in Application", 2000, 6 pages. <https://www51.honeywell.com/sm/em/common/documents/4.2_technical_papers_2000_4.pdf>.
"Development of Heat-dissipating Sheets achieving both Metal-like High Thermal Conductivity and Flexibility", News Release, Hitachi Chemical Co., Ltd., Japan, Jun. 23, 2009, 3 pages. <http://www.hitachi-chem.co.jp/english/information/2009/n_090623.html>.
"Hi-Flow 225FT; Reworkable, Pressure Sensitive Phase Change Material", Product Brochure, The Bergquist Company, Chanhassen, Minnesota, 2008, 1 page. <http://www.bergquistcompany.com/pdfs/dataSheets/PDS_HF_225FT_12.08_E.pdf>.
Christopher O. Muller, "Control of Corrosive Gases to Avoid Electrical Equipment Failure", Purafil, Inc., webpage: www.purafil.com/literature/control-of-corrosive-gases.pdf, 1999, pp. 1-13.
Manuel A. Rivera, "Design Considerations for Reliable Electrical, Control and Instrumentation Systems in Geothermal Power Plants With Emphasis on Hydrogen Sulphide Related Problems", Geothermal Training Programme; United Nations University; 2007, pp. 161-490.
Ezdine Ferjani et al., "Bulk and surface modification of cellulose diacetate based RO/NF membranes by polymethylhydrosiloxane—Preparation and characterization", Desalination, vol. 146, Issues 1-3, 2002, pp. 325-330.
Ronald L. Cicero et al., "Photoreactivity of Unsaturated Compounds with Hydrogen-Terminated Silicon (111)", Langmuir, vol. 16, Issue 13, 2000, pp. 5688-5695.
John H. MacMillan, Ph.D. "Homogeneous Platinum Catalysts", United Chemical Technologies, Inc., 2008, 69 pages.
Rosaria Ciriminna, et al., "Closing the Organosilicon Synthetic Cycle: Efficient Heterogeneous Hydrosilylation of Alkenes over SiliaCat Pt(0)", ACS Sustainable Chemistry & Engineering, 2012, 5 pages.
U.S. Appl. No. 13/283,734, to Boday et al., entitled "Microcapsules Adapted to Rupture in a Magnetic Field", filed Oct. 28, 2011, assigned to International Business Machines Corporation.

(56) References Cited

OTHER PUBLICATIONS

U.S. Appl. No. 14/244,921, to Boday et al., entitled "Microcapsules Adapted to Rupture in a Magnetic Field", filed Apr. 4, 2014, assigned to International Business Machines Corporation.
U.S. Appl. No. 14/244,964, to Boday et al., entitled "Microcapsules Adapted to Rupture in a Magnetic Field", filed Apr. 4, 2014, assigned to International Business Machines Corporation.
U.S. Appl. No. 14/245,074, to Boday et al., entitled "Microcapsules Adapted to Rupture in a Magnetic Field", filed Apr. 4, 2014, assigned to International Business Machines Corporation.
English language machine translation of abstract of JP53-42181 (1978), 1 page.
CAS Registry No. 2530-83-8, SciFinder, American Chemical Society (ACS), 2015, 1 page.
U.S. Appl. No. 13/495,132, to Boday et al., entitled "Thermal Interface Material (TIM) with Thermally Conductive Integrated Release Layer", filed Jun. 13, 2012, assigned to International Business Machines Corporation.
U.S. Appl. No. 15/484,391, to Boday et al., entitled "Thermal Interface Material (TIM) with Thermally Conductive Integrated Release Layer", filed Apr. 11, 2017, assigned to International Business Machines Corporation.
Chen et al., "Pervaporation performance of crosslinked polydimethylsiloxane membranes for deep desulfurization of FCC gasoline," Journal of Membrane Science, vol. 322, 2008, pp. 113-121.

\* cited by examiner

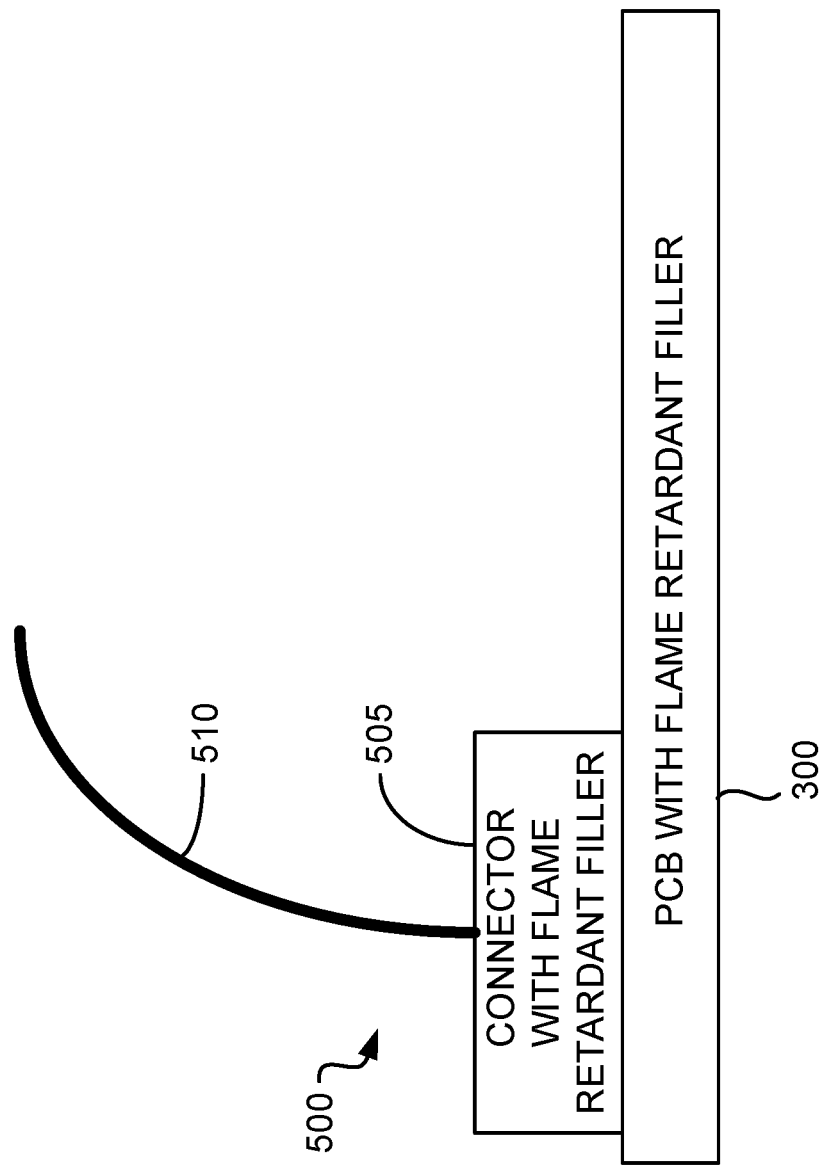

FLAME RETARDANT FILLER

CROSS-REFERENCE TO RELATED APPLICATIONS

This patent application is a divisional application of pending U.S. patent application Ser. No. 15/015,905, filed Feb. 4, 2016, entitled "FLAME RETARDANT FILLER", which is a continuation application of U.S. patent application Ser. No. 14/512,491, filed Oct. 13, 2014, entitled "FLAME RETARDANT FILLER", which is a divisional application of U.S. patent application Ser. No. 13/102,306, filed May 6, 2011, entitled "FLAME RETARDANT FILLER", each of which is hereby incorporated herein by reference in its entirety.

BACKGROUND OF THE INVENTION

1. Field of Invention

The present invention relates in general to the field of flame retardancy. More particularly, the present invention relates to imparting flame retardancy to manufactured articles such as printed circuit boards (PCBs), connectors, and other articles of manufacture that employ thermosetting plastics or thermoplastics.

2. Background Art

In the manufacture of PCBs, connectors, and other articles of manufacture that employ thermosetting plastics (also known as "thermosets") or thermoplastics, incorporation of a filler material as well as a flame retardant is required for rheology control (viscosity, flow, etc.) and ignition resistance, respectively. Typically, both attributes are not found in one material. That is, silica particles are generally the filler of choice for rheology control, whereas brominated organic compounds impart flame retardancy. Consequently, the base material (e.g., epoxy resin for PCBs, and liquid crystal polymer (LCP) for connectors) properties are compromised because a relatively large quantity of both a filler and a flame retardant is necessary to achieve the desired properties.

Therefore, a need exists for an improved mechanism for imparting flame retardancy to manufactured articles such as PCBs, connectors, and other articles of manufacture that employ thermoplastics or thermosets.

SUMMARY OF THE INVENTION

In accordance with the preferred embodiments of the present invention, a flame retardant filler having brominated silica particles, for example, imparts flame retardancy to manufactured articles such as printed circuit boards (PCBs), connectors, and other articles of manufacture that employ thermosetting plastics or thermoplastics. In this example, the brominated silica particles serve both as a filler for rheology control (viscosity, flow, etc.) and a flame retardant. In an exemplary application, a PCB laminate stack-up includes conductive planes separated from each other by a dielectric material that includes a flame retardant filler comprised of brominated silica particles. In an exemplary method of synthesizing the brominated silica particles, a monomer having a brominated aromatic functional group is reacted with functionalized silica particles (the particle surface is functionalized to contain a functional group such as isocyanate, vinyl, amine, or epoxy). Alternatively, a monomer having a brominated aromatic functional group may be reacted with a silane to produce a brominated alkoxysilane monomer, which is then reacted with the surface of silica particles.

BRIEF DESCRIPTION OF THE DRAWINGS

The preferred exemplary embodiments of the present invention will hereinafter be described in conjunction with the appended drawings, where like designations denote like elements.

FIG. 5 is a block diagram illustrating an exemplary connector having a plastic housing that incorporates a flame retardant filler in accordance with the preferred embodiments of the present invention.

DETAILED DESCRIPTION OF THE PREFERRED EMBODIMENTS

Figure 1:
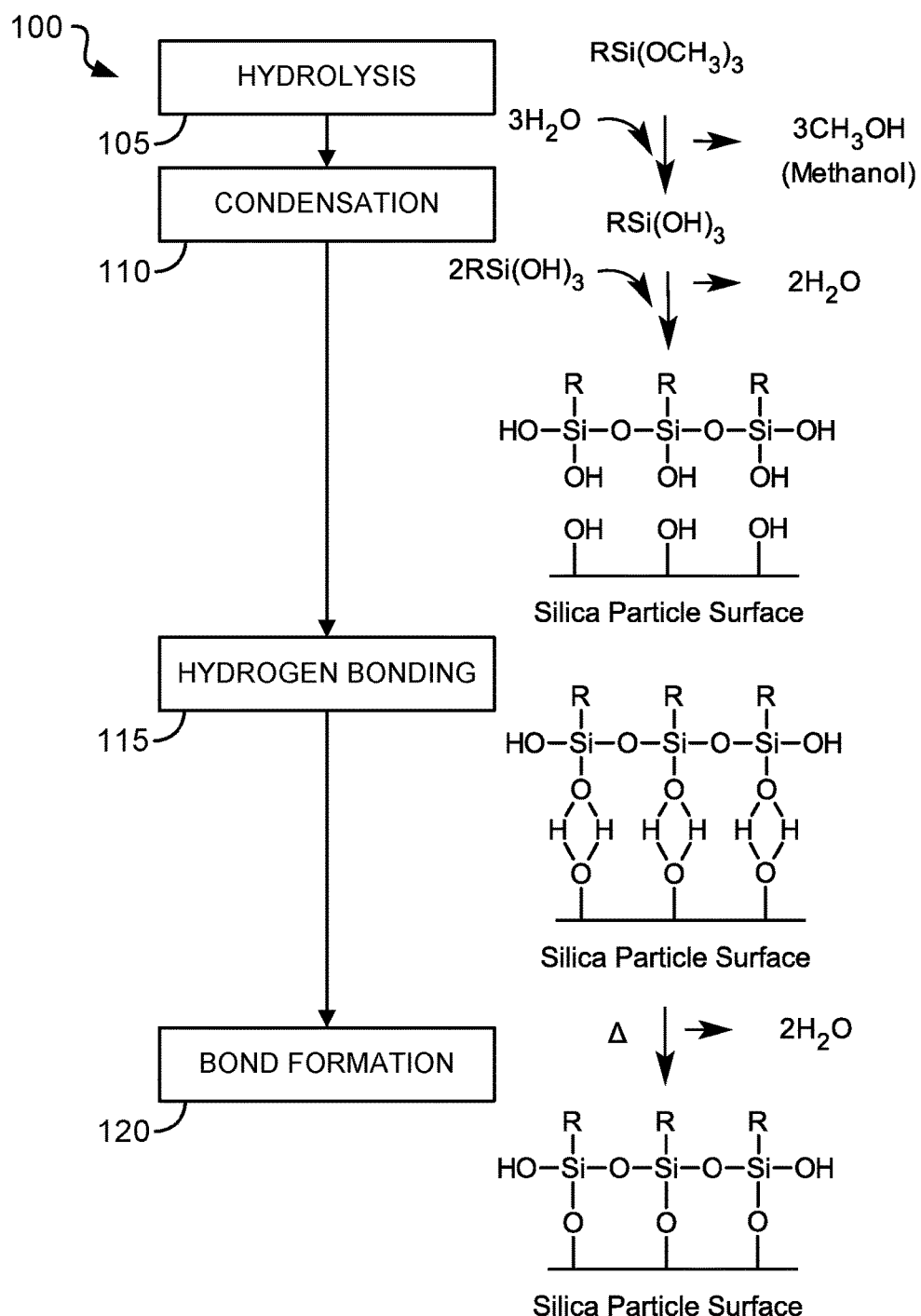
FIG. 1 is a process flow diagram illustrating a method for synthesizing functionalized silica particles to be brominated in accordance with the preferred embodiments of the present invention.

In accordance with the preferred embodiments of the present invention, a flame retardant filler having brominated silica particles, for example, imparts flame retardancy to manufactured articles such as printed circuit boards (PCBs), connectors, and other articles of manufacture that employ thermosetting plastics or thermoplastics. In this example, the brominated silica particles serve both as a filler for rheology control (viscosity, flow, etc.) and a flame retardant. An exemplary printed circuit board (PCB) implementation of the present invention is described below with reference to FIGS. 3 and 4, while an exemplary connector implementation is described below with reference to FIG. 5. However, those skilled in the art will appreciate that the present invention applies equally to any manufactured article that employs thermosetting plastics (also known as "thermosets") or thermoplastics.

As described below, the brominated silica particles may be synthesized by, for example, reacting a monomer having a brominated aromatic functional group and functionalized silica particles (e.g., the particle surface is functionalized to contain a functional group such as isocyanate, vinyl, amine or epoxy). This first pathway to prepare brominated silica particles in accordance with the preferred embodiment of the present invention is exemplified by reaction schemes 1, 3 and 4, below. However, those skilled in the art will appreciate that brominated silica particles in accordance with the preferred embodiments of present invention may be synthesized using other processes and reaction schemes. For example, a monomer having a brominated aromatic functional group may be reacted with a silane to produce a brominated alkoxysilane monomer, which is then reacted with the surface of silica particles to synthesize the brominated silica particles. This second pathway to prepare brominated silica particles in accordance with the preferred embodiment of the present invention is exemplified by reaction scheme 6, below.

Functionalized silica particles from which brominated silica particles in accordance with the preferred embodiments of the present invention are produced may be either obtained commercially or synthesized. Isocyanate functionalized silica particles, for example, are either commercially available or can be readily prepared by reacting an organosilane, such as isocyanate-terminated alkoxysilane with a silica particle. For example, alkoxysilanes or chlorosilanes can be condensed on the surface of a silica particle to yield a silica particle containing numerous pendant functional groups.

Likewise, monomers having a brominated aromatic group suitable for reacting with functionalized silica particles to produce brominated silica particles in accordance with the preferred embodiments of the present invention may be either obtained commercially or synthesized.

While the preferred embodiments of the present invention are described below in the context of a flame retardant filler having bromated silica particles, a flame retardant filler in accordance with the present invention may more generally comprise halogenated silica particles (e.g., chlorinated silica particles) as well as silica particles that incorporate non-halogen (e.g., phosphorous) species that impart flame retardancy. For example, any of a number of organohalogen compounds (OHCs) may be reacted with functionalized silica particles (or, alternatively, the OHC may be reacted with a silane, which then may be reacted with the surface of silica particles) in accordance with the present invention. These OHCs may be either obtained commercially or synthesized.

FIG. 1 is a process flow diagram illustrating a method 100 for synthesizing functionalized silica particles to be brominated in accordance with the preferred embodiments of the present invention. Silica particles are easily functionalized via a silane coupling agent. Use of a vinyl-terminated silane coupling agent, for example, enables the incorporation of a monomer having a brominated aromatic functional group to impart flame retardancy.

Typically, a coupling agent is used to join two disparate surfaces. In the manufacture of printed circuit boards (PCBs), a silane coupling agent is often used to join a varnish coating (e.g., an epoxy-based resin) to a substrate (e.g., glass cloth) to define a laminate, or laminated structure. The silane coupling agent typically consists of an organofunctional group to bind to the varnish coating and a hydrolyzable group that binds to the surface of the substrate. In particular, the alkoxy groups on the silicon hydrolyze to silanols, either through the addition of water or from residual water on the surface of the substrate. Subsequently, the silanols react with hydroxyl groups on the surface of the substrate to form a siloxane bond (Si—O—Si) and eliminate water.

In accordance with the preferred embodiments of the present invention, silane coupling agents suitable for purposes of the present invention include (without limitation) vinyl, isocyanate or amine-terminated trialkoxysilanes. One skilled in the art will appreciate, however, that the silane coupling agent is not limited to an isocyanate, vinyl or amine-terminated trialkoxysilane. As illustrated in FIG. 1, the method 100 begins with the hydrolysis (step 105) of the silane coupling agent, i.e., RSi(OCH$_3$)$_3$, to produce RSi(OH)$_3$. In accordance with the preferred embodiments of the present invention, R is a functional group (e.g., vinyl, isocyanate or amine-terminated) reactive with a monomer having a brominated aromatic functional group. Methanol is a byproduct of the hydrolysis step 105. The method 100 continues with condensation (step 110) of the RSi(OH)$_3$ to produce a compound represented by the following formula.

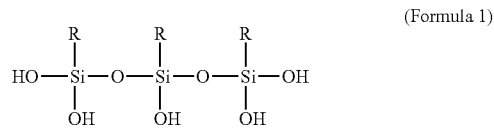

(Formula 1)

Water is a byproduct of the condensation step 110. The method 100 continues with hydrogen bonding (step 115) of the condensate onto the surface of a silica particle to produce a silica particle represented by the following formula.

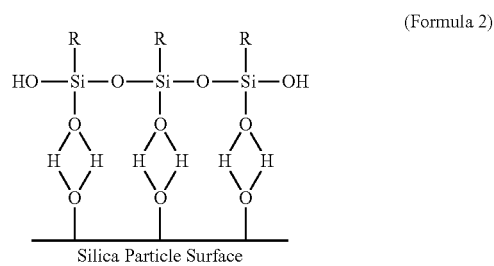

(Formula 2)

The method 100 concludes with bond formation (step 120) through the application of heat to produce a functionalized silica particle represented by the following formula.

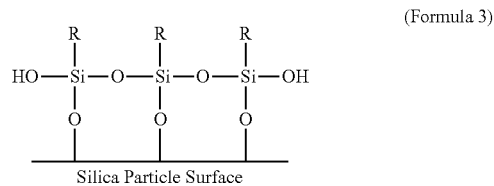

(Formula 3)

Water is a byproduct of the bond formation step 120. Each of these steps (i.e., steps 105-120) is performed using procedures well known to those skilled in the art.

In embodiments described below, synthesis of brominated silica particles in accordance with the present invention is demonstrated through the use of isocyanate functionalized silica particles (e.g., synthesized using a isocyanate-terminated trialkoxysilane), hydrogen functionalized silica particles (e.g., synthesized using a hydrogen-terminated trialkoxysilane), and vinyl functionalized silica particles (e.g., synthesized using a vinyl-terminated trialkoxysilane). However, similar reaction schemes may be employed using, for instance, a glycidylepoxy- or cycloaliphatic epoxy-terminated trialkoxysilane. In this case, the pendant epoxy group can react directly with the hydroxyl group of brominated p-cumylphenol (i.e., an exemplary monomer having a brominated aromatic functional group, discussed below), for example, via suitable catalysts.

The functionalized silica particle shown in FIG. 1 is subsequently reacted with any of a number of reactants to yield either the brominated silica particle, directly, or a precursor that can be brominated via synthetic procedures well known to those skilled in the art. Any of a number of monomers having a brominated aromatic functional group may be used. For example, U.S. Pat. No. 5,777,007 to Kagawa et al., entitled "BROMINATED P-CUMYLPHENOL FLAME-RETARDANTS FOR RESIN COMPOSI- TION", issued Jul. 7, 1998, which is hereby incorporated herein by reference in its entirety, discloses the preparation of brominated p-cumylphenol and its use as a flame retardant for resin compositions. This particular monomer (i.e., brominated p-cumylphenol) is represented by the following formula (where a=1 to 3 and b=1 to 2).

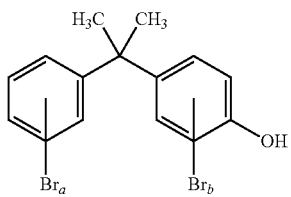

(Formula 4)

A reaction scheme (reaction scheme 1) follows for synthesizing brominated silica particles in accordance with the preferred embodiments of the present invention by reacting isocyanate functionalized silica particles and a monomer having a brominated aromatic functional group. Here too, a=1 to 3 and b=1 to 2.

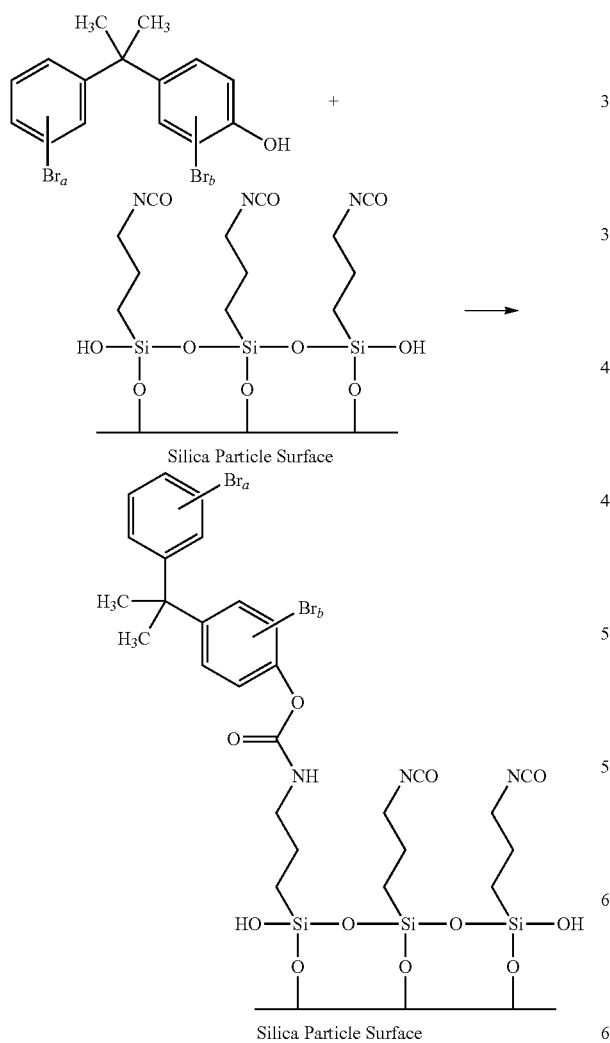

Only a single coupling reaction is illustrated in the above reaction scheme 1 for the sake of clarity. However, it is typically desirable to maximize the Br content of the brominated silica particles by reacting all of the available isocyanate groups. Generally, stoichiometric quantities of the reactants may be used. However, the relative quantity of the reactants may be adjusted to achieve a desired level of Br content of the brominated silica particles. The above reaction scheme 1 is performed at room temperature using conventional procedures well known to those skilled in the art.

A vinyl-terminated monomer having a brominated aromatic functional group for use in accordance with the preferred embodiments of the present invention is represented by the following formula (where a=1 to 3 and b=1 to 2).

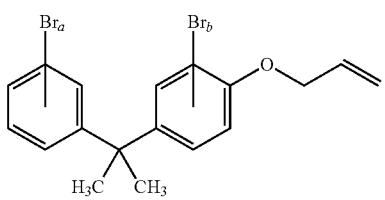

(Formula 5)

A reaction scheme (reaction scheme 2) follows for the preparation of the above vinyl-terminated monomer having a brominated aromatic functional group (formula 5). Here too, a=1 to 3 and b=1 to 2.

(Reaction Scheme 2)

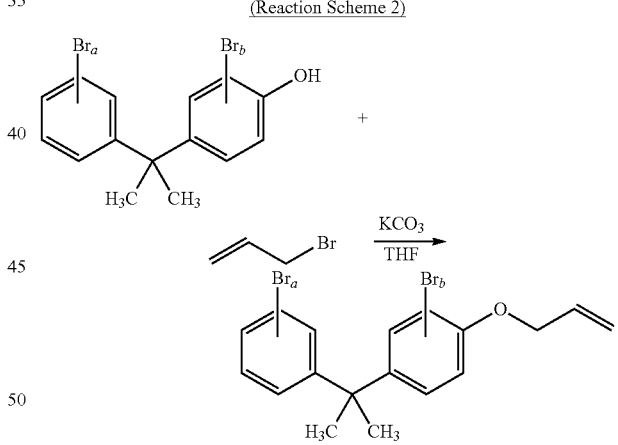

Reaction scheme 2 reacts brominated p-cumylphenol (formula 4) and brominated propylene. Generally, stoichiometric quantities of the reactants may be used. This reaction, which occurs in the presence of potassium carbonate ($KCO_3$) and tetrahydrofuran (THF), is performed at room temperature using conventional procedures well known to those skilled in the art.

A reaction scheme (reaction scheme 3) follows for synthesizing brominated silica particles in accordance with the preferred embodiments of the present invention by platinum catalyzed coupling onto hydrogen functionalized silica particles using the above vinyl-terminated monomer with a brominated aromatic functional group (formula 5). Here too, a=1 to 3 and b=1 to 2.

(Reaction Scheme 3)

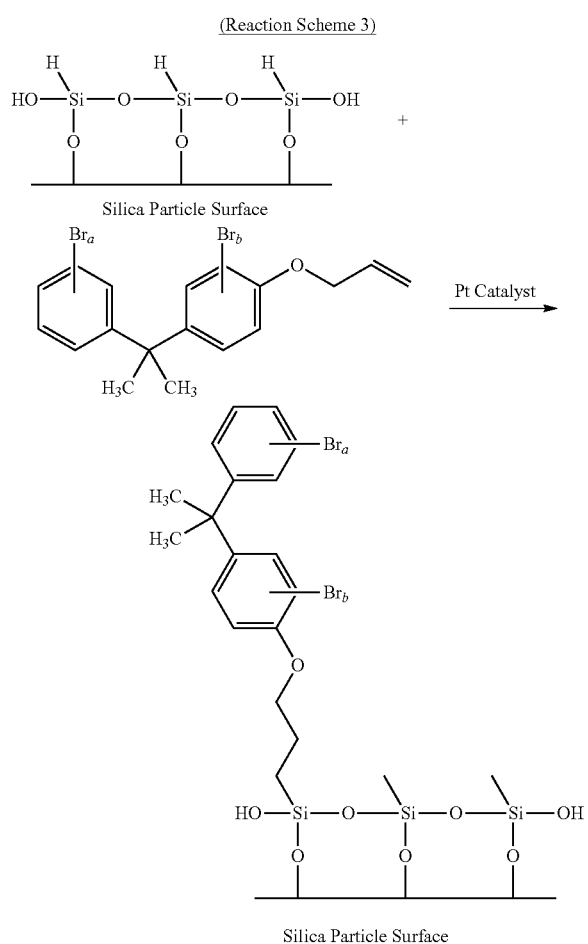

Silica Particle Surface

Only a single coupling reaction is illustrated in the above reaction scheme 3 for the sake of clarity. However, it is typically desirable to maximize the Br content of the brominated silica particles by reacting all of the available hydrogen groups. Generally, stoichiometric quantities of the reactants may be used. However, the relative quantity of the reactants may be adjusted to achieve a desired level of Br content of the brominated silica particles. The above reaction scheme 3 is performed at room temperature using conventional procedures well known to those skilled in the art.

A reaction scheme (reaction scheme 4) follows for synthesizing brominated silica particles in accordance with the preferred embodiments of the present invention by metal metathesized coupling onto vinyl functionalized silica particles using the above vinyl-terminated monomer with a brominated functional group (formula 5).

(Reaction Scheme 4)

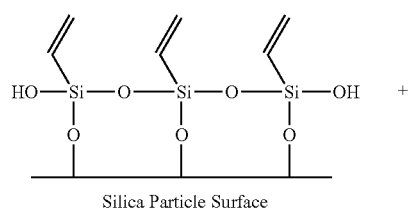

Silica Particle Surface

-continued

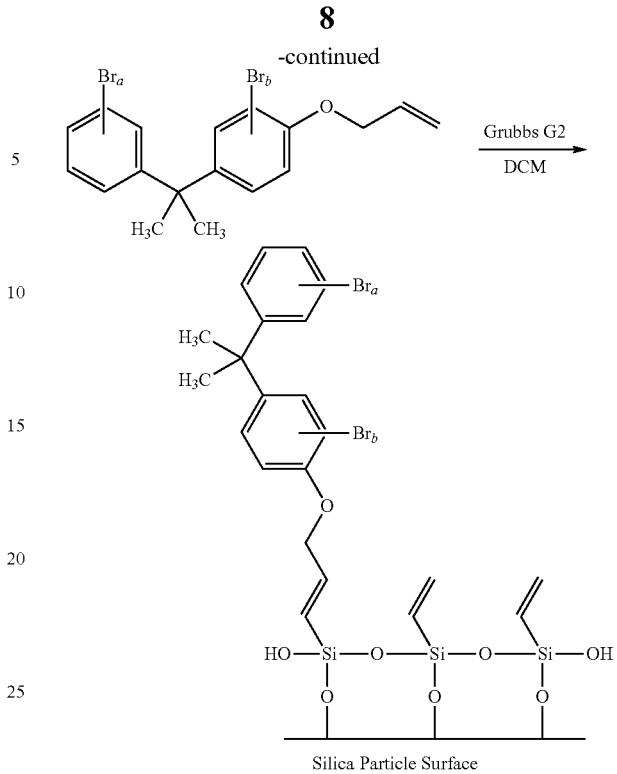

Silica Particle Surface

Only a single coupling reaction is illustrated in the above reaction scheme 3 for the sake of clarity. However, it is typically desirable to maximize the Br content of the brominated silica particles by reacting all of the available vinyl groups. Generally, stoichiometric quantities of the reactants may be used. However, the relative quantity of the reactants may be adjusted to achieve a desired level of Br content of the brominated silica particles. This reaction, which occurs in the presence of Grubbs' second generation (G2) catalyst and dichloromethane (DCM), is performed at room temperature using conventional procedures well known to those skilled in the art.

Although the present invention has been illustrated via the forgoing synthetic pathways, it is understood that any of a number of reaction schemes may be invoked to brominate a silica particle. For instance, the vinyl-terminated silica particle can be modified with allyltriphenyl silane via coupling reaction such as olefin metathesis. A suitable catalytic cycle for olefin metathesis that may be used in this regard is illustrated in FIG. 2.

Figure 2:
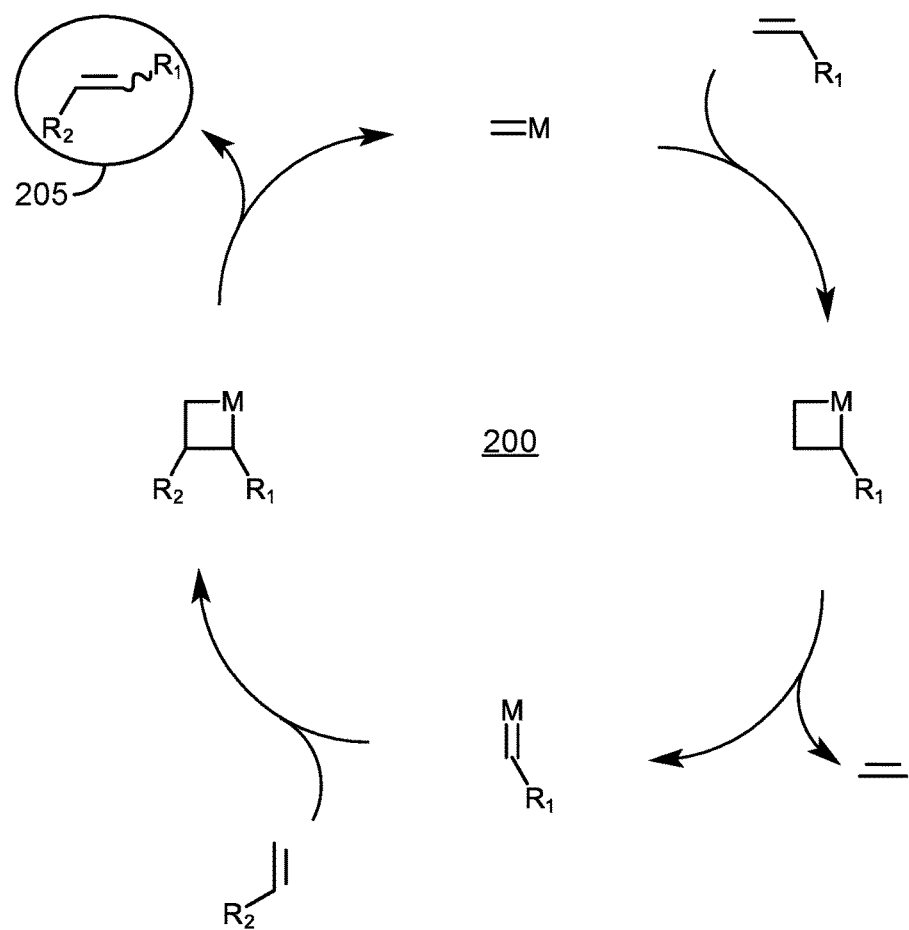
FIG. 2 is a catalytic cycle diagram illustrating an olefin metathesis by which a vinyl-terminated silica particle can be modified with allyltriphenyl silane in accordance with the preferred embodiments of the present invention.

FIG. 2 is a catalytic cycle diagram illustrating an olefin metathesis 200 by which a vinyl-terminated silica particle is modified with allyltriphenyl silane in accordance with the preferred embodiments of the present invention. In FIG. 2, $R_1$ is a vinyl functional triphenyl compound such as triphenylsilane or 1,1-diphenyl-4-pentenylbenzene. $R_2$ is the vinyl functionalized silica particle. M is a metal catalyst suitable for olefin metathesis, such as Grubbs' second generation (G2) catalyst. The product of the coupling reaction is denoted with reference numeral 205.

The product of the coupling reaction 205 is subsequently brominated using n-bromosuccinimide, $Br_2$ or aqueous $KBr_3$. Kumar et al., "Instantaneous, Facile and Selective Synthesis of Tetrabromobisphenol A using Potassium Tribromide: An Efficient and Renewable Brominating Agent", Organic Process Research & Development 2010, Vol. 14, No. 1, 2010, pp. 174-179 (Published on Web Dec. 30, 2009), which is hereby incorporated herein by reference in its entirety, discloses techniques for brominating conventional flame retardants using aqueous KBr₃.

Another example of a monomer having a brominated aromatic functional group for use in accordance with the preferred embodiments of the present invention is a brominated alkoxysilane monomer such as that represented by the following formula.

(Formula 6)

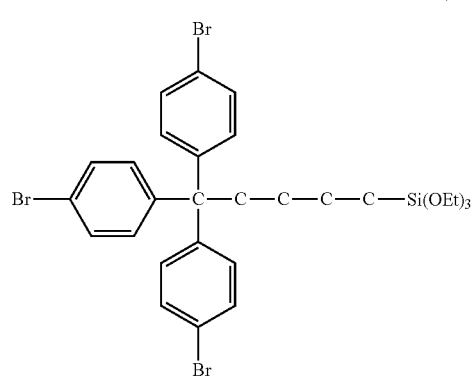

A reaction scheme (reaction scheme 5) follows for synthesizing the above brominated alkoxysilane monomer (formula 6).

(Reaction Scheme 5)

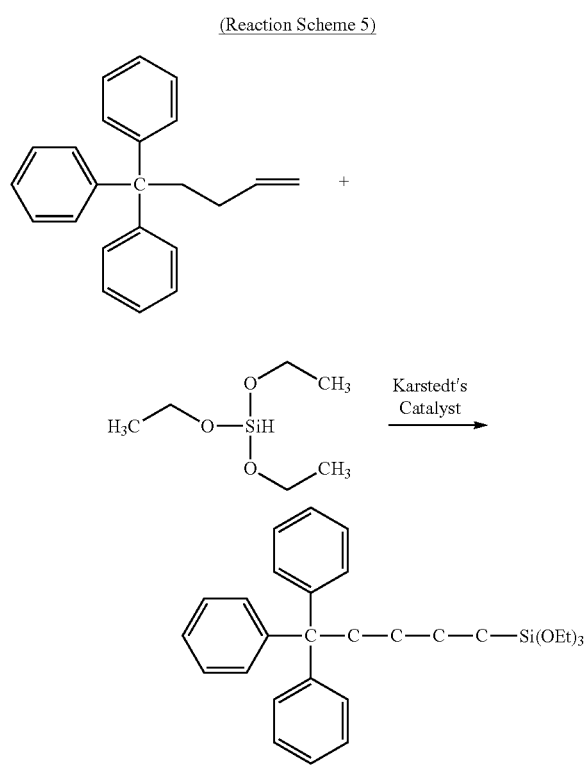

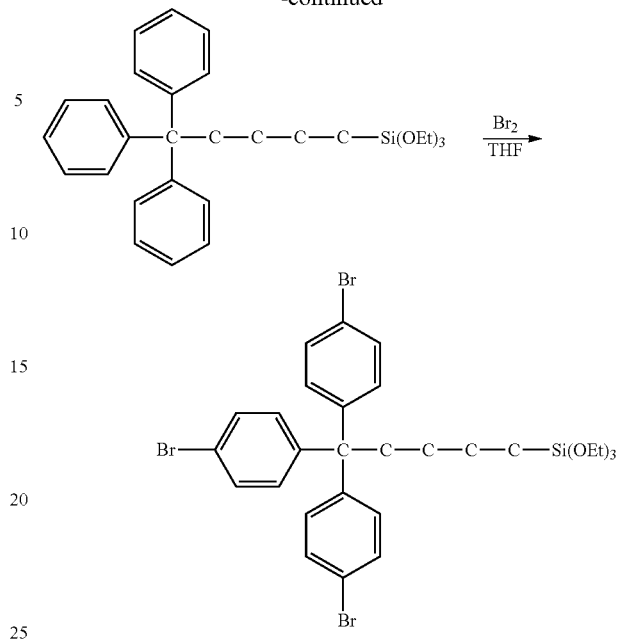

A first reaction step of the above reaction scheme 5 is a coupling reaction that utilizes Karstedt's catalyst. Generally, stoichiometric quantities of the coupling reactants may be used. In a second reaction step of the above reaction scheme 5, the coupled reaction product of the first reaction step is brominated using $Br_2$ in the presence of tetrahydrofuran (THF). To prepare a flame retardant filler, the brominated alkoxysilane monomer would then be reacted with the surface of the silica particle as described for other alkoxysilane monomers.

In another embodiment, tetrabromo bisphenol A (TBBPA) is incorporated onto the silica particle surface by first preparing the (meth)acryloyl derivative, and then reacting that compound with a vinyl-terminated silica particle. In a similar manner, p-cumylphenol may be reacted with (meth)acrylylchloride, and then with a vinyl-terminated silica particle which would subsequently be brominated via any of the commonly employed methods known to those skilled in the art.

As mentioned earlier, in lieu of synthesizing brominated silica particles by reacting a functionalized silica particles and a monomer having a brominated aromatic functional group, the monomer may be reacted with a silane to produce a brominated alkoxysilane monomer, which is then reacted with the surface of silica particles to synthesize the brominated silica particles. This second pathway to prepare brominated silica particles in accordance with the preferred embodiment of the present invention is exemplified by the following reaction scheme (reaction scheme 6) and may be used in lieu of the first pathway (exemplified in reaction schemes 1, 3 and 4, above).

(Reaction Scheme 6)

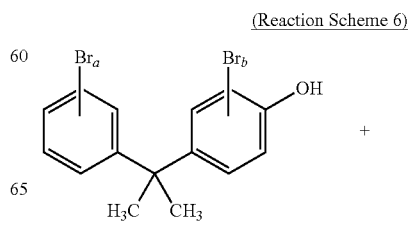

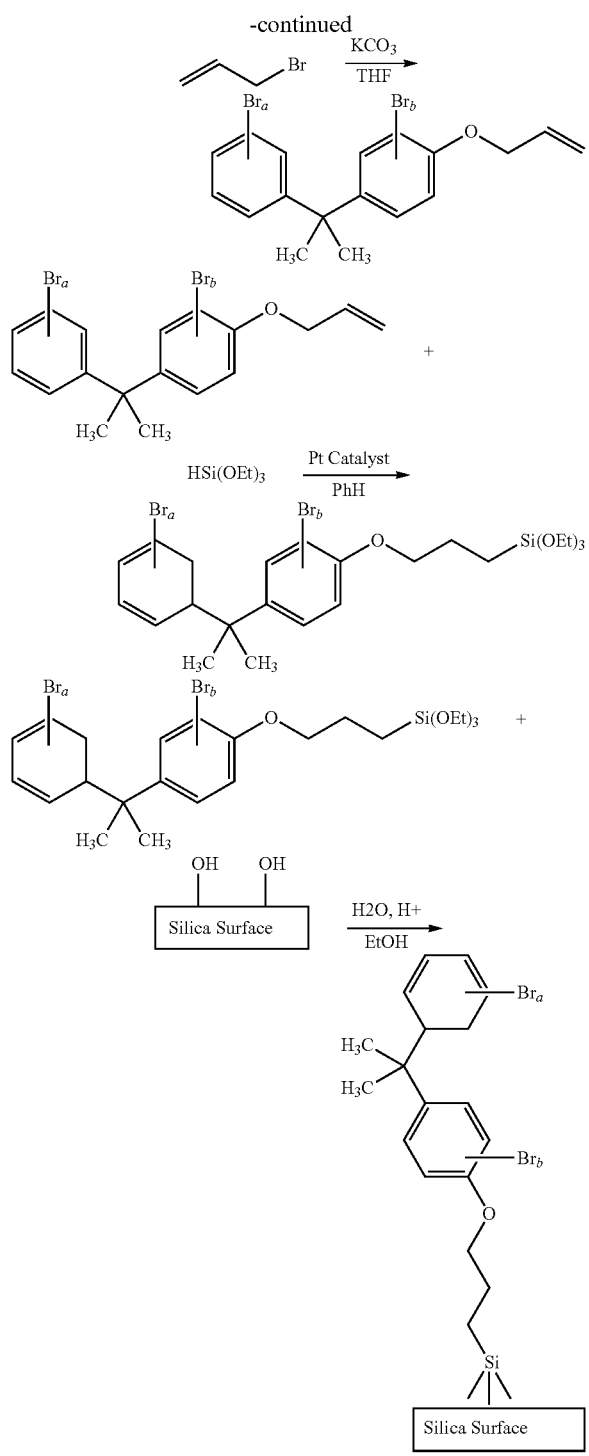

In the above reaction scheme 6, a=1 to 3 and b=1 to 2. A first reaction step of the above reaction scheme 6 reacts brominated p-cumylphenol and brominated propylene to produce a vinyl-terminated monomer having a brominated aromatic functional group. This first reaction step is identical to reaction scheme 2, above. A second reaction step of the above reaction scheme 6 produces a brominated alkoxysilane monomer by platinum catalyzed coupling of the product of the first reaction step and a silane. Generally, stoichiometric quantities of the coupling reactants may be used. In a third reaction step of the above reaction scheme 6, the brominated alkoxysilane monomer product of the second reaction step is reacted with the silica particle surface to produce a brominated silica particle. The above reaction scheme 6 is performed using conventional procedures well known to those skilled in the art.

Figure 3:
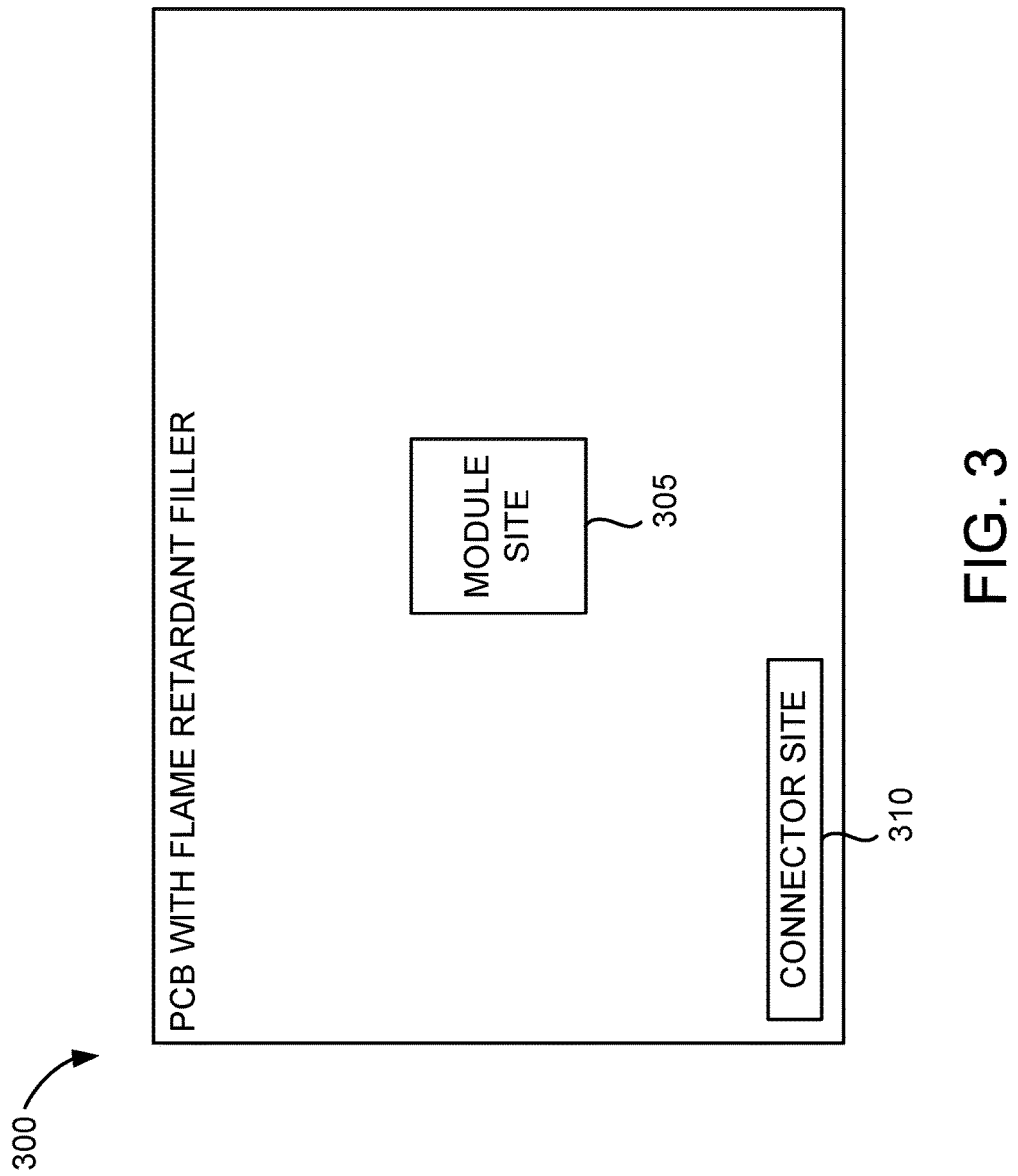
FIG. 3 is a block diagram illustrating an exemplary printed circuit board (PCB) having layers of dielectric material that incorporate a flame retardant filler in accordance with the preferred embodiments of the present invention.
Figure 4:
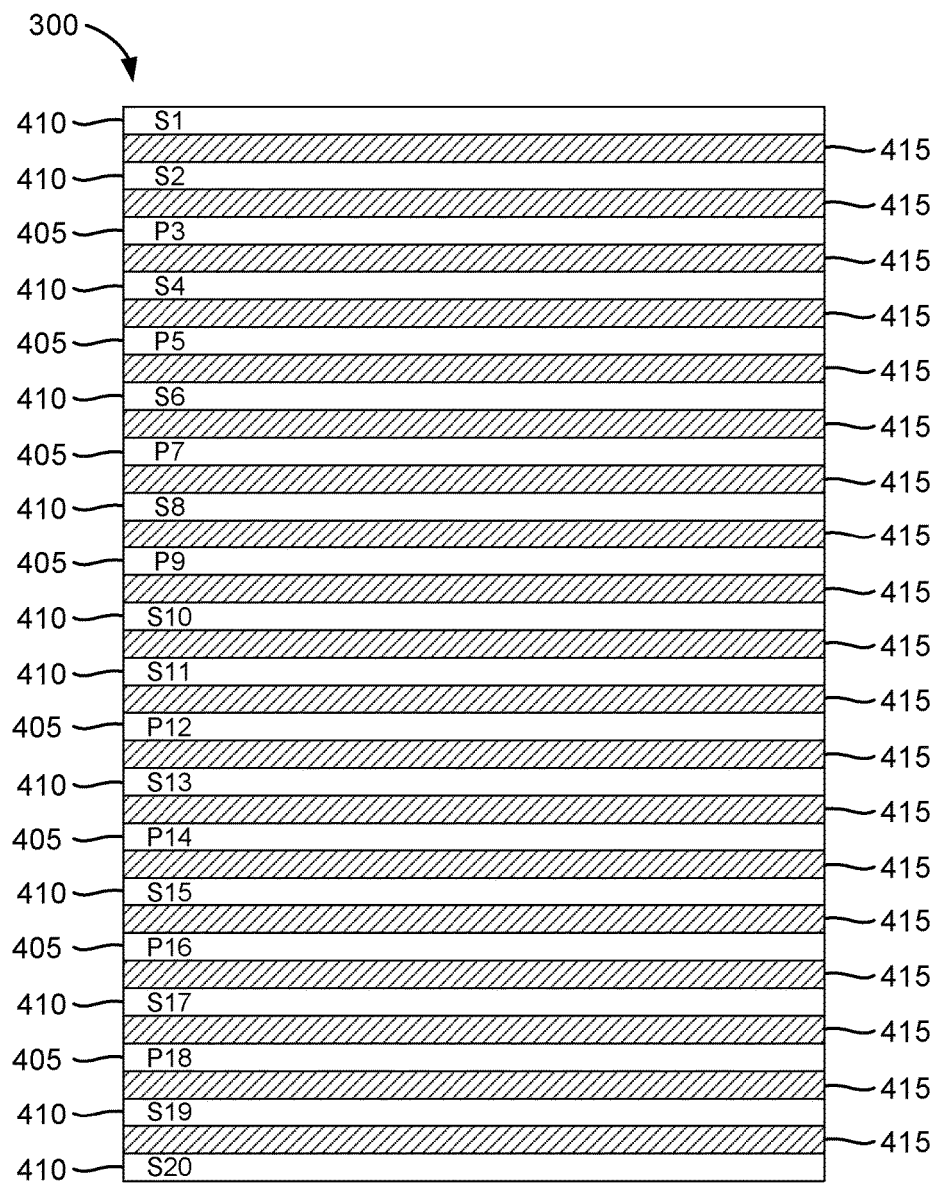
FIG. 4 is a block diagram illustrating an exemplary laminate stack-up of the PCB shown in FIG. 3.

FIG. 3 is a block diagram illustrating an exemplary printed circuit board (PCB) 300 having layers of dielectric material that incorporate a flame retardant filler in accordance with the preferred embodiments of the present invention. In the embodiment illustrated in FIG. 3, the PCB 300 includes one or more module sites 305 and one or more connector sites 310. FIG. 4 is a block diagram illustrating an exemplary laminate stack-up of the PCB 300 shown in FIG. 3. The configuration of the PCB 300 shown in FIG. 3 and its laminate stack-up shown in FIG. 4 are for purposes of illustration and not limitation.

As illustrated in FIG. 4, the laminate stack-up of the PCB 300 includes conductive planes (e.g., voltage planes 405 and signal planes 410) separated from each other by dielectric material 415. For example, the voltage planes 405 include power planes P3, P5, P7, . . . , while the signal planes 410 include signal planes S1, S2, S4, . . . . In accordance to the preferred embodiments of the present invention, one or more of the layers of the dielectric material 415 includes a filler of brominated silica particles that imparts flame retardancy.

Each layer of dielectric material (e.g., the dielectric material 415) of a PCB typically includes a varnish coating (e.g., an FR4 epoxy resin, a bismaleimide triazine (BT) resin, or a polyphenylene oxide/trially-isocyanurate (PPO/TAIC) interpenetrating network) applied to a glass fiber substrate (e.g., woven glass fiber) having its surface modified by a silane coupling agent (e.g., typically consists of an organo-functional group to bind to the varnish coating and a hydrolyzable group that binds to the surface of the glass fiber substrate, such as vinylbenzylaminoethylaminopropyl-trimethoxysilane or diallylpropylisocyanurate-trimethoxysilane). In accordance with the preferred embodiments of the present invention, a flame retardant filler comprised of brominated silica particles, for example, is incorporated into the varnish coating to impart flame retardancy.

FIG. 5 is a block diagram illustrating an exemplary connector 500 having a plastic housing 505 that incorporate a flame retardant filler in accordance with preferred embodiments of the present invention. In the embodiment illustrated in FIG. 5, the connector 500 in configured to make electrical contact with the connector site 310 (shown in FIG. 3) of the PCB 300. Also in the embodiment illustrated in FIG. 5, the connector 500 includes a cable 510. The configuration of the connector 500 shown in FIG. 5 is for purposes of illustration and not limitation.

In accordance with the preferred embodiments of the present invention, a flame retardant filler comprised of brominated silica particles, for example, is incorporated into the plastic housing 505 to impart flame retardancy. The base material of the plastic housing 505 may be, for example, liquid crystal polymer (LCP) or any suitable thermoplastic or thermoset to which the filler is added.

One skilled in the art will appreciate that many variations are possible within the scope of the present invention. Thus, while the present invention has been particularly shown and described with reference to preferred embodiments thereof, it will be understood by those skilled in the art that these and other changes in form and details may be made therein without departing from the spirit and scope of the present invention.

What is claimed is:
1. A flame retardant filler, comprising:
halogenated silica particles, wherein the halogenated silica particles include a halogenated aromatic functional group, wherein the halogenated silica particles include particles made by a method comprising:

providing functionalized silica particles;
halogenating the functionalized silica particles to produce halogenated silica particles, wherein the step of halogenating the functionalized silica particles includes the step of reacting a monomer having a brominated aromatic functional group and the functionalized silica particles, wherein the monomer is selected from a group of monomers represented by the following formulas:

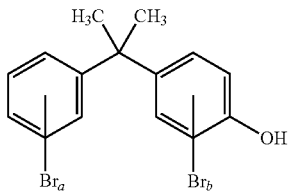

wherein a is an integer of 1 to 3, and wherein b is an integer of 1 to 2,

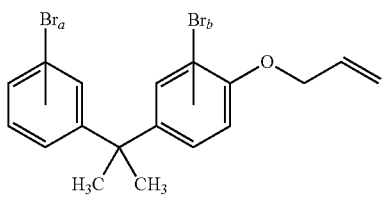

wherein a is an integer of 1 to 3, and wherein b is an integer of 1 to 2,
and combinations thereof.

2. The flame retardant filler as recited in claim 1, wherein the halogenated silica particles include particles represented by the following formula:

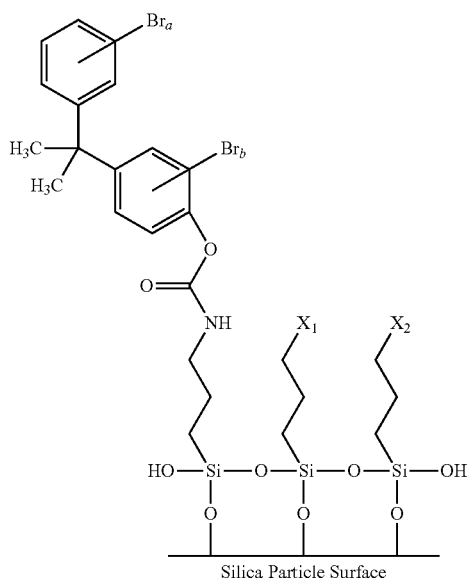

wherein a is an integer of 1 to 3, wherein b is an integer of 1 to 2, and wherein $X_1$ and $X_2$ is either an isocyanate group NCO or a group represented by the formula:

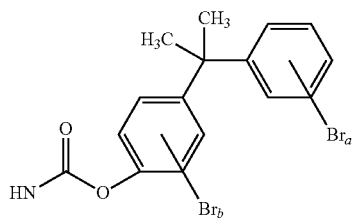

wherein a is an integer of 1 to 3, and wherein b is an integer of 1 to 2.

3. The flame retardant filler as recited in claim 1, wherein the halogenated silica particles include particles represented by the following formula:

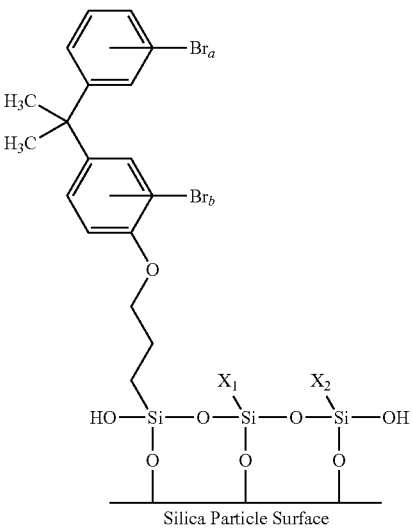

wherein a is an integer of 1 to 3, wherein b is an integer of 1 to 2, and wherein $X_1$ and $X_2$ is either a hydrogen atom or a group represented by the formula:

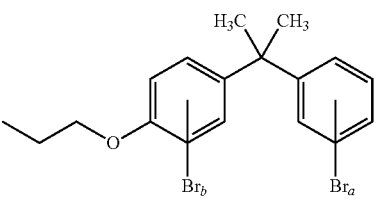

wherein a is an integer of 1 to 3, and wherein b is an integer of 1 to 2.

4. The flame retardant filler as recited in claim 1, wherein the halogenated silica particles include particles represented by the following formula:

15

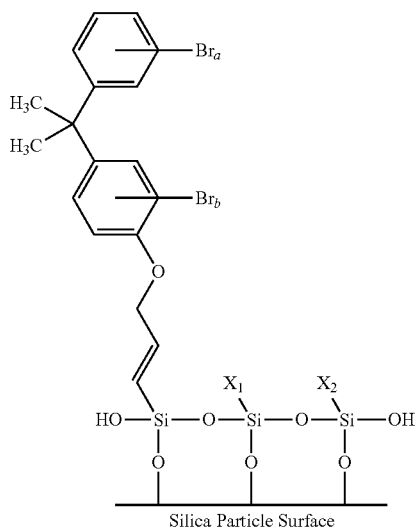

wherein a is an integer of 1 to 3, wherein b is an integer of 1 to 2, and wherein $X_1$ and $X_2$ is either a vinyl group or a group represented by the formula:

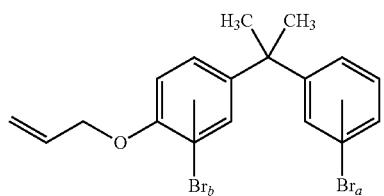

wherein a is an integer of 1 to 3, and wherein b is an integer of 1 to 2.

5. A flame retardant filler, comprising:
halogenated silica particles, wherein the halogenated silica particles include a halogenated aromatic functional group, wherein the halogenated silica particles include particles made by a method comprising:
providing functionalized silica particles;
halogenating the functionalized silica particles to produce halogenated silica particles, wherein the step of halogenating the functionalized silica particles includes the step of reacting a monomer having a brominated aromatic functional group and the functionalized silica particles, wherein the monomer is selected from a group of monomers represented by the following formulas:

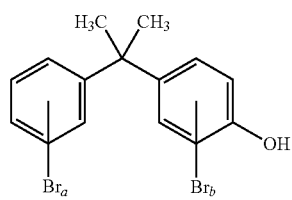

wherein a is an integer of 1 to 3, and wherein b is an integer of 1 to 2,

16

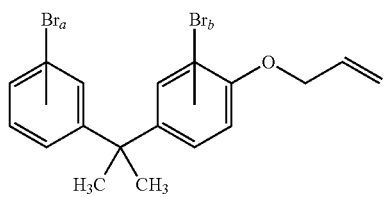

wherein a is an integer of 1 to 3, and wherein b is an integer of 1 to 2,

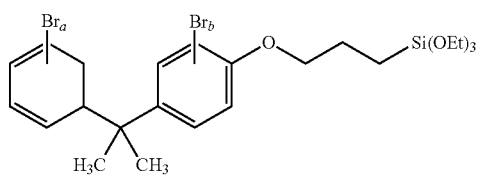

wherein a is an integer of 1 to 3, and wherein b is an integer of 1 to 2,

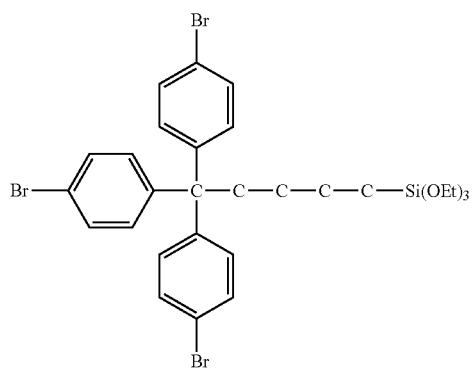

and combinations thereof.

6. A flame retardant filler, comprising:
halogenated silica particles, wherein the halogenated silica particles include particles made by a method comprising:
providing functionalized silica particles;
halogenating the functionalized silica particles to produce halogenated silica particles, wherein the step of halogenating the functionalized silica particles includes the step of reacting a monomer having a brominated aromatic functional group and the functionalized silica particles, wherein the monomer is selected from a group of monomers represented by the following formulas:

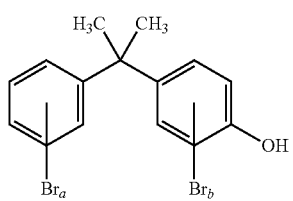

wherein a is an integer of 1 to 3, and wherein b is an integer of 1 to 2,

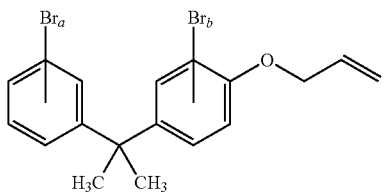

wherein a is an integer of 1 to 3, and wherein b is an integer of 1 to 2,

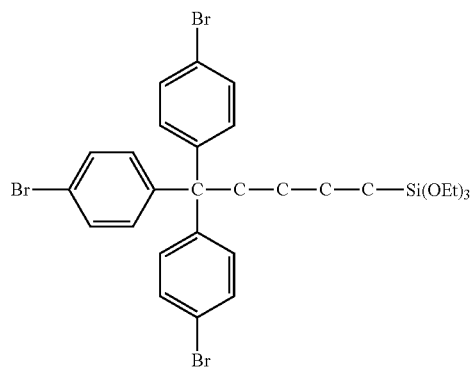

and combinations thereof.

7. The flame retardant filler as recited in claim 6, wherein the halogenated silica particles include particles represented by the following formula:

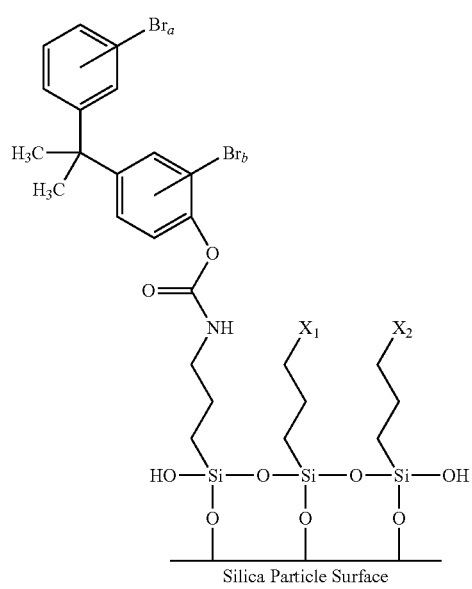

wherein a is an integer of 1 to 3, wherein b is an integer of 1 to 2, and wherein $X_1$ and $X_2$ is either an isocyanate group NCO or a group represented by the formula:

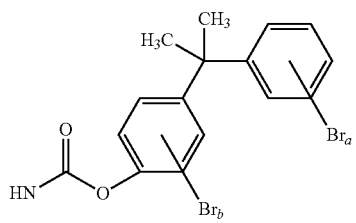

wherein a is an integer of 1 to 3, and wherein b is an integer of 1 to 2.

8. The flame retardant filler as recited in claim 6, wherein the halogenated silica particles include particles represented by the following formula:

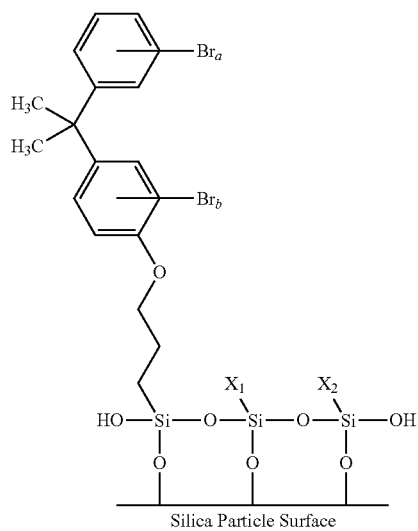

wherein a is an integer of 1 to 3, wherein b is an integer of 1 to 2, and wherein $X_1$ and $X_2$ is either a hydrogen atom or a group represented by the formula:

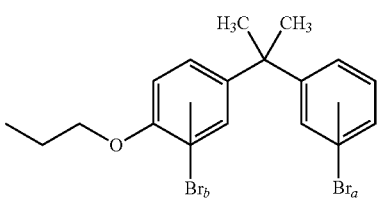

wherein a is an integer of 1 to 3, and wherein b is an integer of 1 to 2.

9. The flame retardant filler as recited in claim 6, wherein the halogenated silica particles include particles represented by the following formula:

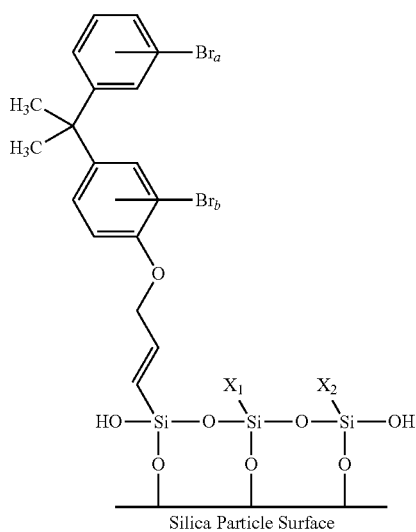
wherein a is an integer of 1 to 3, wherein b is an integer of 1 to 2, and wherein $X_1$ and $X_2$ is either a vinyl group or a group represented by the formula:
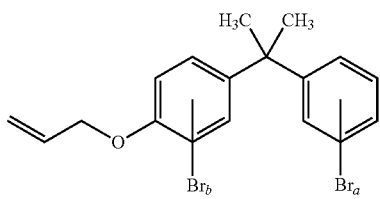
wherein a is an integer of 1 to 3, and wherein b is an integer of 1 to 2.
* * * * *